United States Patent [19]

Geddes et al.

[11] Patent Number: 4,827,935
[45] Date of Patent: May 9, 1989

[54] DEMAND ELECTROVENTILATOR

[75] Inventors: Leslie A. Geddes; Charles F. Babbs, both of W. Lafayette; William D. Vorhees, III, Lafayette; Joe D. Bourland, W. Lafayette, all of Ind.

[73] Assignee: Purdue Research Foundation, West Lafayette, Ind.

[21] Appl. No.: 855,321

[22] Filed: Apr. 24, 1986

[51] Int. Cl.$^4$ .............................................. A61N 1/36
[52] U.S. Cl. .................................. 128/419 G; 128/723
[58] Field of Search ................... 128/419 G, 716, 421, 128/723, 783, 419 R

[56] References Cited

U.S. PATENT DOCUMENTS

| | | | |
|---|---|---|---|
| 2,532,788 | 12/1950 | Sarnoff | 128/419 G |
| 2,664,880 | 1/1954 | Wales, Jr. | 128/419 G |
| 2,711,729 | 6/1955 | Hofmann | 128/419 G |
| 3,077,884 | 2/1963 | Bartrow et al. | |
| 3,802,417 | 4/1974 | Lang | 128/716 |
| 3,818,900 | 6/1974 | Nickel | |
| 4,141,356 | 2/1979 | Smargiassi | |

FOREIGN PATENT DOCUMENTS

| | | | |
|---|---|---|---|
| 8301742 | 5/1983 | PCT Int'l Appl. | |
| 8600234 | 1/1986 | PCT Int'l Appl. | 128/419 G |
| 1399717 | 6/1975 | United Kingdom | |

OTHER PUBLICATIONS

I. Satoh, J. F. Hogan, W. W. L. Glenn, and Y. Fujii, "a Demand Diaphragm Pacemaker", *Trans. Am. Soc. Artif. Intern. Organs*, vol. XXIII (1977).

S. Goldenthal, "Bilateral and Unilateral Activation of the Diaphragm in the Intact Human," Connecticut Medicine (Apr., 1961).

G. W. Holmes, M.D., W. B. Buckingham, M.D., D. W. Cugell, M.D., K. Kirchner, M.D., "Electric Stimulation of Breathing in Chronic Lung Diseases," J.A.M.A. (Mar., 1958).

L. Geddes, W. D. Voorhees, III, C. F. Babbs, "Abstracts from Purdue Conference on CPR-Electroventiliation," Journal of Emergency Medicine, vol. 2, No. 4, (Jul. 1984).

L. A. Geddes, H. E. Hoff, D. M. Hickman and A. G. Moore, "the Impedance Pneumograph," Aerospace Medicine (Jan. 1962).

M. Noshiro, S. Suzuki, A. Ishida, "Method of Electrophrenic Respiration for Producing a Natural Respiratory Flow Rate Using Feedback Control of Tidal Volume Waveform", *Medical & Biological Engineeering & Computing* (Nov., 1982).

*Primary Examiner*—Ruth S. Smith
*Attorney, Agent, or Firm*—Barnes & Thornburg

[57] ABSTRACT

A demand electroventilator for monitoring and stimulating the respiration of a patient operates in a manner analogous to the operation of a demand cardiac pacemaker for monitoring and stimultating the heart when needed. The demand electroventilator has a pair of stimulating electrodes for placement on the chest of the patient and a pair of monitoring electrodes for placement on the patient's chest. The demand electroventilator also has a monitoring module connected to the monitoring electrodes, a stimulating module connected to the stimulating electrodes and a control module connected to the stimulating and monitoring modules. The monitoring module generates a signal related to the respiration of the patient which the control module interprets and causes the stimulating module to apply a train of electrical pulses having durations of 0.1 msec or less to the patient to stimulate respiration when needed.

20 Claims, 4 Drawing Sheets

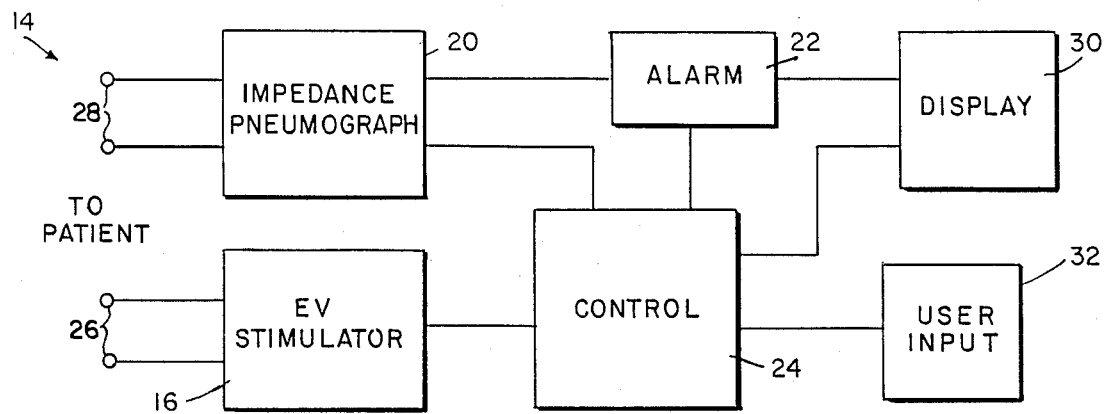
FIG. 8
FIG. 9
PRIOR ART
FIG. 10
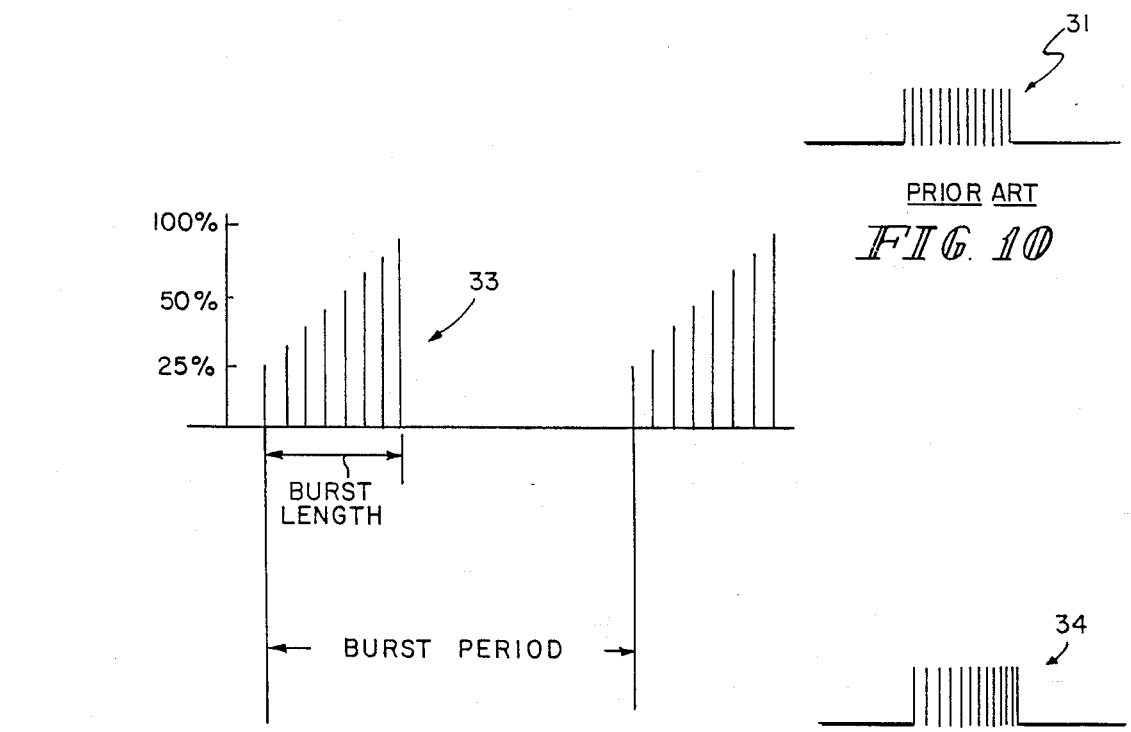
FIG. 11
FIG. 12

DEMAND ELECTROVENTILATOR

This invention relates to the stimulation of respiration and more particularly to an improved apparatus and method for monitoring respiration and stimulating respiration when necessary analogous to a demand cardiac pacemaker which monitors and stimulates the heart when necessary.

Various techniques for monitoring respiration are known. There is, for example, the impedance pneumograph which utilizes a pair of electrodes attached to the chest wall of a patient. The electrodes detect changes in transthoracic impedance which occur during inhalation and exhalation. L. A. Geddes, H. E. Hoff, D. M. Hickman, and A. G. Moore, "The Impedance Pneumograph," Aerospace Medicine (January 1962). There are also the pneumograph, pneumotachograph, spirometer, and negative pressure transducer.

It is also known to use electrical stimuli to produce inhalation. For example, in the late 1800's it was known to use an induction coil stimulator to contract the muscles of inspiration by phrenic-nerve stimulation in the neck and also with transchest electrodes.

Inducing respiration by electrical stimuli provides significant advantages over commonly used ventilators. Traditional ventilators respirate a patient by forcing air into the patient's lungs through the nose, mouth, or both. This creates a positive intrathoracic pressure. Positive intrathoracic pressure inhibits blood flow back to the heart from the lungs. This effect decreases cardiac output and, in cases of seriously ill patients, can contribute to degradations in the patient's condition.

Inducing respiration by electrical stimuli, on the other hand, respirates the patient by stimulating the muscles, nerves, or both, which cause natural breathing. Thus, using electrical stimuli to induce respiration causes negative intrathoracic pressure during inhalation which is the natural condition.

It is advantageous to use a sequence of short duration pulses when stimulating respiration. This has been termed "electroventilation." L. A. Geddes, W. D. Voorhees III, C. R. Babbs, "Electroventilator," Abstracts from the Fifth Purdue Conference on CPR and Defibrillation, July 1984. Long duration pulses stimulate the heart as well as respiration and can cause arrythmias in the heart.

It is known that proper placement of electrodes on the chest wall is crucial for optimum stimulation of respiration. As is known, it is normally necessary to induce only inhalation to stimulate respiration. Exhalation typically occurs naturally after inhalation and requires no stimulus. However, improper placement of electrodes on the chest wall will not only prevent optimum stimulation of respiration, but can induce exhalation instead of inhalation or can simultaneously stimulate nerves/muscles responsible for both inhalation and exhalation.

It is also known to combine a respiration monitor with a respiration stimulator to stimulate respiration only when necessary. This type of apparatus will monitor a patient's respiration and when breathing irregularities are detected such as the absence of respiration for a predetermined period of time, a stimulus will be applied to the patient to stimulate respiration. Such a system is shown in Great Britain Patent No. 1,399,717 ("G.B. No. '717"). However, G.B. No. '717 discloses using one or more needle pulses having a duration of substantially 10 msec. As discussed, pulses of this duration have a significant effect upon the heart and introduce a substantial possibility of causing arrythmias in the heart.

A problem suffered by heretofore known electrical respiration stimulators is that the stimuli used to induce inhalation causes a sudden intake of breath similar to a gasp. Although this stimulates respiration, it does so in less than an optimum manner. When sudden inhalation is induced in this manner, the tidal volume (volume of air inhaled) is less than that which would be inhaled with a smooth, gradual inhalation.

It is an object of this invention to provide an electroventilator which optimally stimulates inhalation respiration by producing a smooth, gradual, even intake of breath to achieve optimum tidal volume.

It is another object of this invention to provide a demand electroventilator which monitors respiration and optimally stimulates respiration when breathing irregularity or apnea is detected in a manner analogous to the action of a demand cardiac pacemaker.

In an embodiment of the invention, an electroventilator is provided to optimally stimulate respiration by the application of a ramped pulse train to the chest wall. Preferably, the pulses in the pulse train have a duration of 0.1 msec. or less and have a frequency of 20-60 pulses/sec. The pulse train preferably has a pedestal at its beginning of 25% of the final current at the end of the pulse train and the last pulse in the train has an amplitude of 100% of the peak current required, an illustrative peak current being in the range of 100-200 ma. Shorter duration pulses require higher currents. In an embodiment of the invention, each pulse has a duration in the range of 0.01 msec to 0.1 msec.

In an embodiment of the invention, an electroventilator is provided to optimally stimulate respiration by the application of a frequency modulated pulse train to the chest wall. Preferably, the pulses have a duration of 0.1 msec. or less and a D.C. amplitude in the range of 50 ma-200 ma. In an embodiment of the invention, each pulse has a duration of 0.01 msec. to 0.1 msec. and the frequency varies between 10 Hz and 100 Hz.

In an embodiment of the invention, a demand electroventilator for monitoring and stimulating the respiration of a patient operates in a manner analogous to the operation of a demand cardiac pacemaker for monitoring and stimulating the heart when needed. The demand electroventilator has a pair of stimulating electrodes for placement on the chest of the patient and a pair of monitoring electrodes for placement on the patient's chest. The demand electroventilator also has a monitoring module connected to the monitoring electrodes, a stimulating module connected to the stimulating electrodes and a control module connected to the stimulating and monitoring modules. The monitoring module generates a signal related to the respiration of the patient which the control module interprets and causes the stimulating module to apply a train of electrical pulses having durations of 0.1 msec or less to the patient to stimulate respiration when needed.

Additional features and advantages of the invention will become apparent to those skilled in the art upon consideration of the following detailed description of a preferred embodiment, exemplifying the best mode of carrying out the invention as presently perceived. The detailed description particularly refers to the accompanying figures in which:

FIG. 8 is a block diagram of a demand electroventilator constructed in accordance with this invention;

FIG. 9 is a graph showing the increased frequency of muscle action potentials during inspiration;

FIG. 10 shows a prior art train of 60 HZ, 0.05 msec. pulses having equal amplitude;

FIG. 11 shows a linearly ramped train of electrical pulses used to stimulate respiration in accordance with this invention; and FIG. 12 shows a frequency modulated train of electrical pulses used to stimulate respiration in accordance with this invention.

Figure 1:
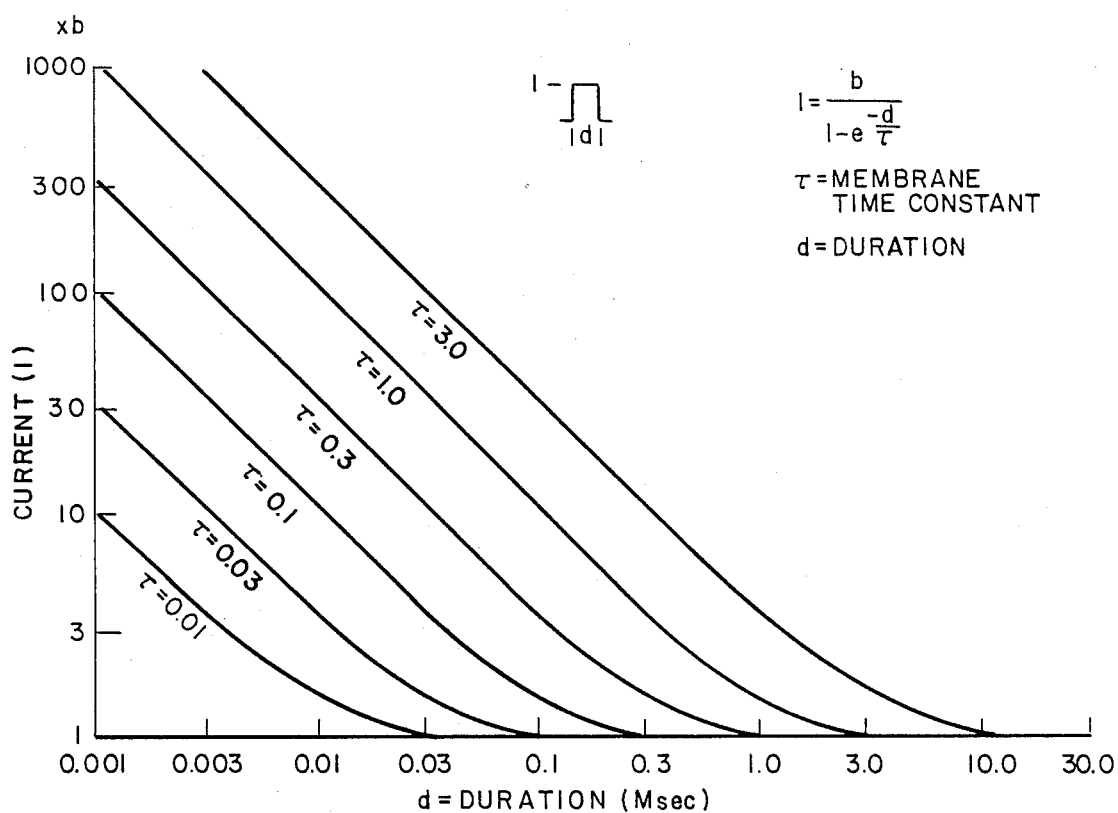
FIG. 1 is a graph showing the threshold strength-duration curves for tissues having different membrane time constants.

In an embodiment of the invention, a demand electroventilator is provided. The demand electroventilator has means for monitoring the respiration of a patient and means for stimulating respiration. The demand electroventilator further includes means for computing the respiration level of the patient based upon the monitored respiration and determining whether to cause respiration stimulation based upon the computed respiration. The respiration monitoring means and the respiration stimulating means are both coupled to the computing means. The respiration stimulating means stimulates respiration by generating an electrical pulse train which is applied to the patient wherein each pulse has a duration of 0.1 msec. or less. In one embodiment, the preferred pulse train is a ramped pulse train. Illustratively, the ramped pulse train is a linearly ramped pulse train having a pedestal, that is, a beginning amplitude of 25% of the final current at the end of the pulse train. Illustratively, the pulse train has an ending amplitude of 100% of the peak current, illustratively 100 ma.-200 ma. Shorter duration pulses require higher currents as shown in FIG. 1. Each pulse illustratively has a duration in the range of 0.01 msec to 0.1 msec. The repetition rate of the pulses in the pulse train is preferably in the range of 20 pulses/sec to 60 pulses/sec.

In another embodiment, the pulse train is a frequency modulated pulse train wherein the frequency varies in the range of 10 pulses/sec. to 100 pulses/sec. Illustratively, each pulse has a duration in the range of 0.01 msec. to 0.1 msec. The pulses preferably have an amplitude in the range of 100 ma.-200 ma. D.C.

Respiration can be monitored by any one of several techniques. Four instruments commonly used to record respiration are the pneumograph, pneumotachograph, spirometer and negative pressure transducer. Any one of these instruments can be used to provide the monitoring means of this invention.

It is sometimes preferred to monitor respiration by using a non-invasive technique. This can be done by using an Impedance Pneumograph such as described by L. A. Geddes, H. E. Hoff, D. M. Hickman, and A. G. Moore "The Impedance Pneumograph," Aerospace Medicine pp. 28-33 (January 1962).

Another technique for non-invasively monitoring respiration would be to use a latex tube filled with conducting gel placed around the thorax as described in Geddes & Baker, "Principle of Applied Biomedical Instrumentation," (Wiley, 1975). As the chest expands, the length of the tube increases and its cross-sectional diameter decreases. Since the impedance is rho L/A, where rho is the resistivity of the gel, L the length of the tube and A the cross-sectional area of the tube, inspiratory effort will raise the impedance by increasing L and decreasing A. In such an electrolytic strain guage, a 1% increase in length produces a 2% increase in impedance. Alternatively, a conducting elastomer could be used which increases its resistance as its stretches. Other types of known chemical respiratory sensors could also be used including end-tidal $CO_2$ monitors or pressure based monitors.

Breathing results from the action of three different muscle groups expanding and contracting the chest cavity. These muscle groups are the diaphragm, the intercostal muscles, and what are known as accessory muscles of respiration, principally the anterior neck muscles and abdominal muscles. Quiet breathing results mainly from alternate contraction and relaxation of the diaphragm and intercostal muscles.

The tidal volume of air inhaled is directly related to the expansion of the chest cavity. The effectiveness of the diaphragm in changing the dimension of the chest is related, in part, to the strength of its contraction. The strength of contraction is a function of the number of motor units activated and of the synchronization and frequency of their discharge.

The diaphragm is enervated by the phrenic nerves. The intercostal muscles are enervated by the intercostal nerves. The anterior scalene and other accessory muscles are enervated by the long thoracic nerve. Electroventilation works by directly or indirectly stimulating any or all of the above muscles. In the context of this invention, indirect stimulation of a muscle refers to stimulating the muscle by stimulating its associated nerve.

The essential requirements for a stimulus are abruptness of onset, adequate intensity and duration. These three features are embodied in the basic law of excitation, which expresses itself as the strength-duration curve (a plot of the lowest (threshold) current required to elicit a response in the tissue as a function of pulse duration). The law of excitation is as follows:

$$I = \frac{b}{1 - e^{-d/t}}$$

where d is the stimulus duration and t is the membrane time constant (t=RC) which is a property of the tissue being stimulated, R and C being the membrane resistance and capacitance. The rheobase current b is the threshold current required for an infinitely long duration stimulus. The rheobase current depends on electrode size and distance from the excitable tissue.

Strength-duration curves for tissues of different membrane time constants are shown in FIG. 1. The vertical axis current is normalized by dividing by the rheobase current. As shown by FIG. 1, the strength-duration curves for different tissues have the same form, the difference being the duration where the current required for stimulation increases above rheobasic value with decreasing pulse duration. For a motor nerve, the membrane time constant is 0.1 msec and for mammalian myocardium, it is 2 msec. Thus, with a short-duration pulse, the threshold for myocardial stimulation is much higher than that for motor nerves when the rheobase currents are equal.

Rheobase currents depend on electrode geometry rather than tissue properties. The motor nerves of the respiratory muscles are relatively superficial and current from a skin-surface electrode gains easy access to them. Since the heart is deeper within the thorax, current must flow through high resistivity lung tissue to reach it. Thus, the rheobase current (b) required to stimulate myocardium is many times higher than that for stimulating superficial motor nerves. This difference provides a further margin of safety for electroventilation.

Figure 2:
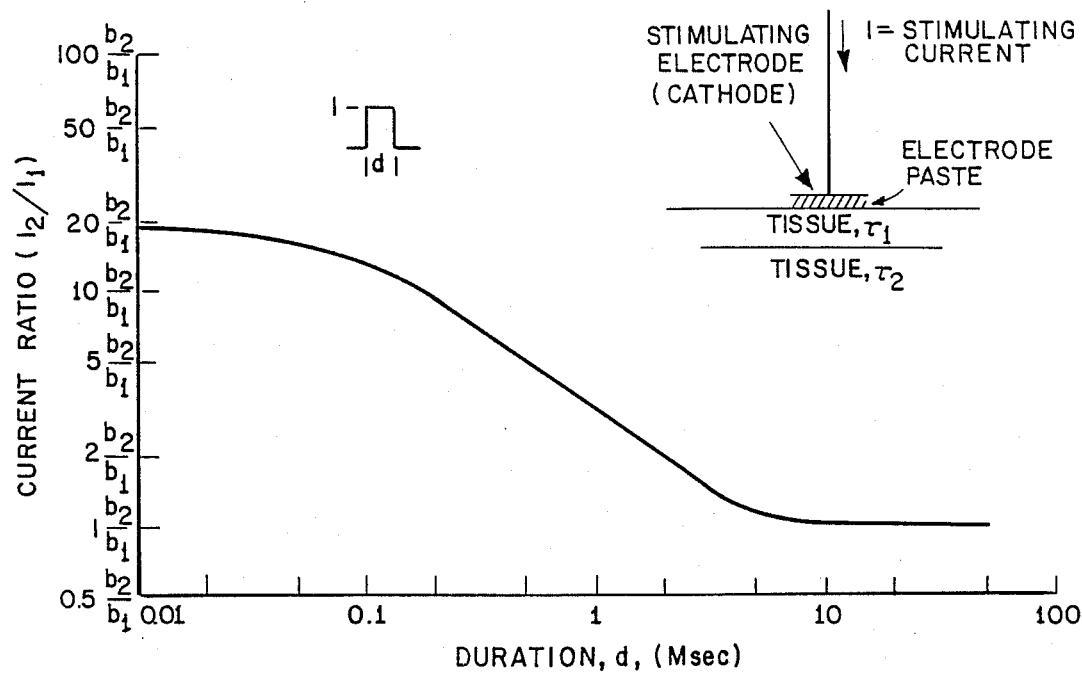
FIG. 2 is a graph showing the ratio of current required to stimulate deeply-lying tissue to the current required to stimulate superficial tissue.

To illustrate the facts pertinent to stimulation of deep-lying tissue, it is useful to consider a two compartment model consisting of two layers of excitable tissue, each having its own membrane constant. Referring to FIG. 2, the ratio of current ($I_2$) required to stimulate deep-lying tissue to the current ($I_1$) required to stimulate superficial tissue for such a model is shown. The membrane time constant and rheobase current of the overlying tissue (1) are $t_1$ and $b_1$, respectively, and the corresponding quantities for the deep-lying tissue (2) are $t_2$ and $b_2$. Thus, $$I_1 = b_1/(1 - e^{-d/t_1})$$

and $$I_2 = b_2/(1 - e^{-d/t_2})$$

and

To achieve electroventilation without cardiac stimulation, an essential feature of this invention, the ratio $I_2/I_1$ should be as large as possible, that is $$\frac{I_2}{I_1} = \frac{b_2 (1 - e^{-d/t_2})}{b_1 (1 - e^{-d/t_1})}$$

should be maximized.

Evaluation of this expression shows that for an infinitely short-duration stimulus, the ratio of $I_2/I_1$ is $b_2/b_1$. The rheobase current $b_2$ will always be much larger than $b_1$ because the superficial tissue is closer to the stimulating electrode. Therefore, to keep the ratio $b_2/b_1$ as large as possible, it is essential that the stimulating electrode be placed so that the superficial tissue (e.g. respiratory motor nerves and muscles) can be stimulated with the least current.

The ratio $I_2/I_1$ also depends upon stimulus duration, as well as $b_2/b_1$. In a particular case, the ratio will depend on the values for $t_1$ and $t_2$. $t_2$ is about 2 msec for heart muscle. $t_1$ is about 0.1 msec for motor nerves. Therefore, it is possible to evaluate the ratio $I_2/I_1$ over a range of durations by entering these values into the expression for current ratio. Therefore:

$$\frac{I_2}{I_1} = \frac{b_2 (1 - e^{-d/2})}{b_1 (1 - e^{-d/0.1})}$$

FIG. 2 shows that the ratio of the two currents increases with decreasing duration, irrespective of the ratio of the rheobase current ($b_2/b_1$). This indicates that a short-duration stimulus should be chosen for electroventilation. FIG. 2 shows that the ratio $I_2/I_1$ is a maximum for durations in the 0.01-0.05 msec duration region. In this region, the ratio is about 20 $b_2/b_1$, $b_2$ being the rheobase current for myocardial stimulation and $b_1$ being that for respiratory motor-nerve stimulation. Although the rheobase current $b_1$ has never been determined for chest electrodes used for ventilation, the inventors estimate that $b_2/b_1$ is about twenty-five. Therefore, the ratio of cardiac stimulation current to that required to excite the respiratory motor nerves is about $20 \times 25 = 500$, which provides a substantial safety margin.

Proper location of the stimulating electrodes on the chest wall is also crucial to achieve optimum stimulation of respiration by electroventilation. Optimum location can be determined experimentally in a manner similar to that discussed below for dogs. The optimum location of the electrodes on humans is expected to be analogous to that found for dogs.

Electroventilation was used to produce artificial respiration in six pentobarbital-anesthetized dogs in which arterial pressure, the electrocardiogram (ECG), oxygen saturation, and the volume of air inspired were recorded. Blood pressure was monitored via a fluid-filled catheter placed in a femoral artery and connected to a Statham P23Db transducer. The volume of air breathed was recorded from an oxygen-filled spirometer containing a carbon-dioxide absorber. An electronically derived signal, proportional to spirometer volume, was inscribed on a graphic record.

Prior to applying electroventilation, respiratory arrest was produced by stimulating the afferent vagal fibers to simulate activation of the Hering-Breuer stretch receptors in the lungs. Selective afferent vagal stimulation was accomplished by exposing the right and left vagal trunks in the neck, attaching encircling bipolar electrodes, and tightly ligating the nerve distal to the electrodes to eliminate cardiac effects.

The chest was mapped with 1-cm diameter electrodes to find the optimum location for producing inspiration. Then, 3-cm diameter, stainless steel electrodes were applied to the optimum location on the left and right chest, and artificial ventilation was produced in by delivering rhythmic bursts of short-duration stimuli to these electrodes.

Figure 3:
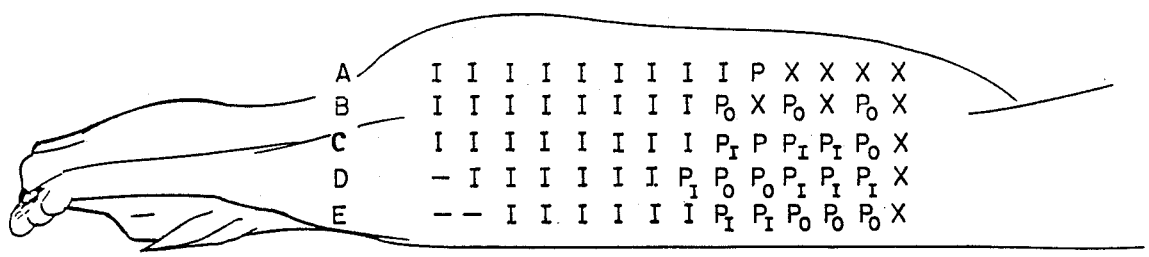
FIG. 3 is a side perspective view of a dog showing regions on the dog chest where stimulation with electrodes produces inspiration, expiration, and paradoxical breathing.

The thorax of each dog was shaved, and a grid of points ($1 \times 1$ inch) was marked with an indelible pen. Stimulating electrodes (1-cm diameter) were held bilaterally over each point, and 1-second bursts of 100 usec. stimuli (with a frequency of 60 pulses/second) were applied. At each point on the chest, the current was increased to obtain a response. The response at each point was marked I for inspiration, X for expiration and P for paradoxical motion. Paradoxical motion describes the motion which occurs when inhalatory and exhalatory muscles are contracted simultaneously. The paradoxical regions were further divided to indicate whether the net effect was zero tidal volume ($P_0$), net inspiratory ($P_I$), or net expiratory ($P_x$). FIG. 3 illustrates these regions on the dog's chest and demonstrates that inspiration is produced with upper-chest electrodes.

Next, the optimum inspiratory points were located. These are defined as the sites where the maximum volume of air is inspred per milliampere of current. The volume of air inspired was measured with a spirometer connected to the cuffed endotracheal tube.

Figure 4:
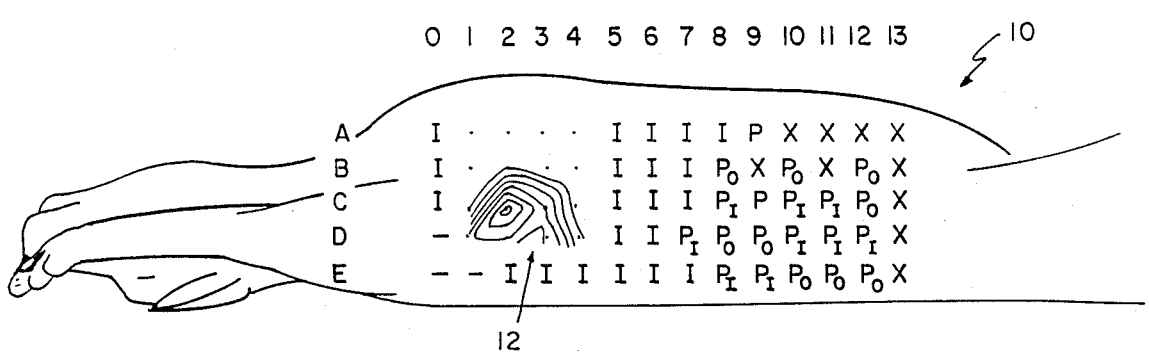
FIG. 4 is a side perspective view of a dog showing a region of electroventilation contours on the dog's chest wall.
Figure 5:
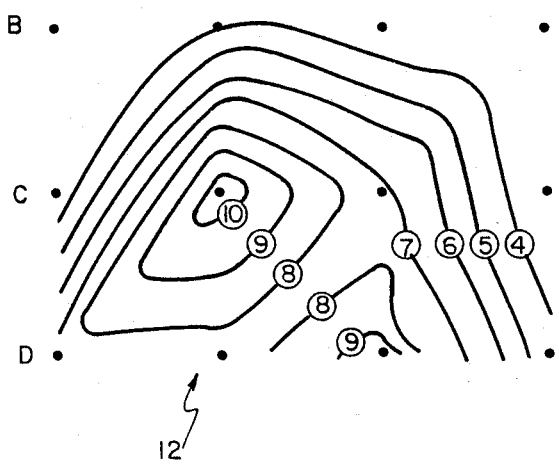
FIG. 5 is an enlarged view of the electroventilation contour region of FIG. 4.

FIG. 4 shows a region of electroventilation contours 12 on the chest of a dog 10. FIG. 5 shows electroventilation contour region 12 in greater detail. The numbers on the contours in FIG. 5 represent ml of air inspired per milliampere of stimulating current. The optimum site (10) is slightly anterior to a midaxillary line and at about the level of the fourth rib. This point was similar in most dogs; although it was 2 to 3 cm more anterior in a few. The coefficient (ml/mA) varied considerably among the dogs, ranging from 2 to 10 ml/mA for the stimulus parameters used.

Figure 6:
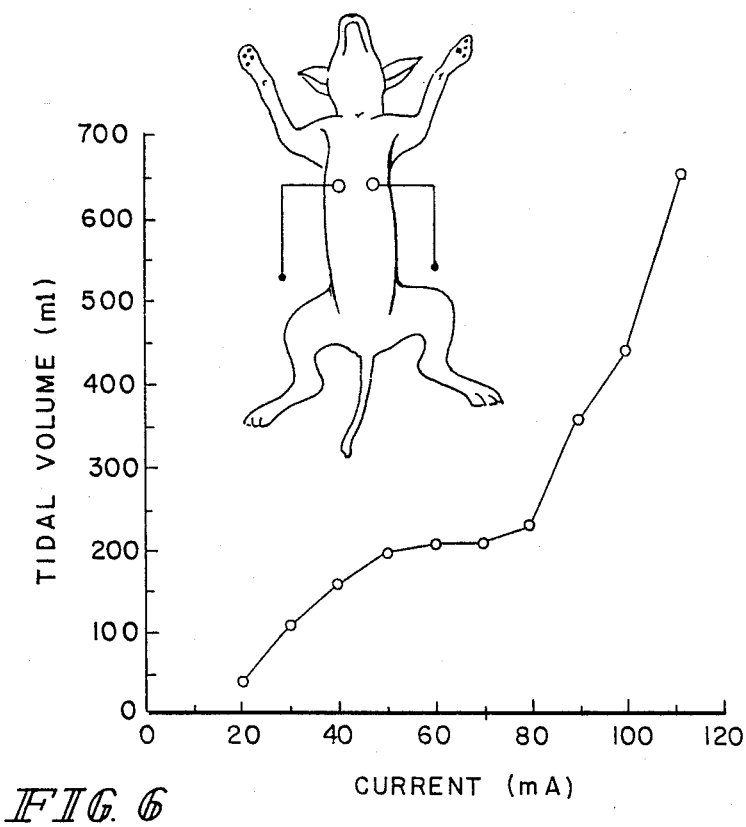
FIG. 6 is a graph showing the volume of air moved versus stimulating current with the use of transaxillary electrodes.

With electrodes at the optimum sites on the dog's chest, the volume of air inspired was measured for 1-second pulse trains (100 usec pulses at a frequency of 60 pulses/second) at different current levels. FIG. 6 presents the results in a typical animal and shows that the volume of air inspired increases with increasing current. This animal exhibited a spontaneous tidal volume of 150 ml and the same volume was achieved with stimuli having a current of about 40 mA. As the current is increased, the volume of air inspired increased dramatically, ultimately reaching a tidal volume of 650 ml. No cardiac arrhythmias were noted during this experiment.

Figure 7:
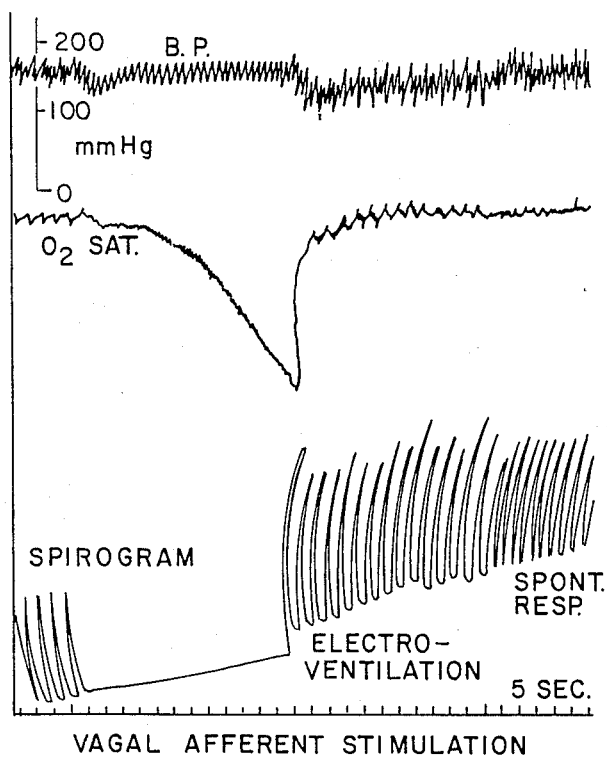
FIG. 7 is a graph showing blood pressure, oxygen saturation and tidal volume under control conditions; respiratory arrest, electroventilation and spontaneous breathing.

Although the foregoing illustrates the movement of air into and out of the trachea, the value of any artificial-respiration system lies in its ability to oxygenate the blood. To demonstrate the ability of electroventilation to oxygenate the blood, oxygen saturation was recorded continuously with a flow-through oximeter in an arteriovenous shunt. FIG. 7 illustrates a typical record. On the left, the animal was breathing spontaneously. In the center, respiratory arrest was induced by afferent vagal stimulation and maintained until oxygen saturation fell by about 20%. At this point, electroventilation was applied. Within about 5 seconds (two to three breaths), the oxygen saturation returned to the control level. After about 1 minute of electroventilation, respiratory arrest and electroventilation were discontinued, and the dog resumed spontaneous breathing at a slightly higher rate and with a slightly reduced tidal volume, but with no change in oxygen saturation.

Referring to FIG. 8, a demand electroventilator constructed in accordance with this invention is shown. Electroventilator 14 illustratively includes a stimulator module 16, an impedance pneumographic module 20, an alarm module 22, and a control module 24. Impedance pneumographic module 20 monitors respiration by impedance pneumography.

The impedance pneumograph operates on the principle that a volume change in the chest cavity, such as that which occurs during inhalation or exhalation, produces a corresponding change in transthoracic impedance. Electrodes are affixed to the right and left side of the chest wall, preferably at the level of the 4th to 6th ribs in the mid axillary line, and a 20 khz signal applied. These electrodes are then used to monitor the impedance change due to inhalation and exhalation, their preferred location being more caudal than the electrodes used for stimulation.

Stimulator module 16 has a current source output circuit capable of producing pulse trains. The duration of each pulse can illustratively be selected to be from 0.01 msec to 0.1 msec. The contours of the pulse trains can also be selected.

A pair of stimulating electrodes 26 are affixed to the chest wall of a patient (not shown). Stimulating electrodes 26 are coupled to stimulator module 16 and apply the pulse trains to the chest of the patient.

A pair of monitoring electrodes 28 are also affixed to the chest wall of the patient (not shown) and are coupled to impedance pneumographic module 20. Impedance pneumographic module 20 stimulates electrodes 28 at an appropriate frequency, illustratively 20 kHz, to optimally detect changes in transthoracic impedance due to inhalation and exhalation. Although it is desirable in many instances to have separate stimulating and monitoring electrodes, it should be understood that stimulating electrodes 26 and monitoring electrodes 28 could be electrically connected and so combined to form a single thoracic pair.

To monitor and stimulate respiration using only one set of electrodes, impedance pneumographic module 20 exploits the fact that stimulator module 16 has a current source output. This type of output circuit permits the application of a low-level 20 kHz sinusoidal signal to stimulating electrodes 26 for the measurement of the transthoracic impedance increase that occurs with inspiration at the same time that pulse trains are being applied to stimulating electrodes 26. Impedance pneumograph module 20 also has a constant-current (high-impedance) output circuit. By monitoring the 20 kHz sinusoidal voltage developed across stimulating electrodes 26, or monitoring electrodes 28 as the case may be, a signal is derived which is indicative of inspiration.

Illustratively, impedance pneumographic module 20 is disabled for 0.4–0.5 seconds when stimulator module 16 is applying a pulse train ("EV stimulation") to stimulating electrodes 26 to induce inspiration ("EV breath"). In another embodiment, narrow band filtering is included in impedance pneumographic module 20 to permit measurement of the impedance change during an EV breath. Alternatively, stimulus module 16 can be configured to produce a low intensity pulse train which is utilized to measure the transthoracic impedance change that results from inspiration. In this embodiment, when EV stimulation is applied to electrodes 26, the gain of impedance pneumographic module 20 is automatically scaled down by the ratio of the EV current used to produce inspiration divided by the low level EV current. This signal can also serve as a monitor of the effectiveness of electroventilation and as the input to alarm module 22 and control module 24.

Alarm module 22 senses when transthoracic impedance becomes too high, indicating that an electrode has become disconnected or has poor contact with the skin and generates an alarm signal to indicate a system failure. Alarm module 22 also senses when the increase in thoracic impedance during electroventilation falls below a reference value and generates an alarm signal to indicate ineffective electroventilation. A suitable display or displays 30 and means 32 for user input of control variables for controlling electroventilator 14 are coupled to control module 24.

Control module 24 implements demand electroventilation. It takes data from impedance pneumographic module 20 and determines the ventilation rate and ventilation volume index (time integral of change in impedance). If the impedance signal indicates bradypnea or hypoventilation, and electroventilator 14 is in the demand mode, control module 24 will initiate an EV breath and cause the current and intensity of the pulse train output by stimulator module 16 to be adjusted to within a safe level until a predetermined sensed respiratory signal is obtained. Control module 24 is also settable to permit a weaning mode, similar to the demand mode, in which an electroventilation stimulus is interposed in the patient's sensed pattern of breathing if adequate ventilatory vigor or rate, as judged by the impedance signals, is not present.

Illustratively, control module 24 can be programmed so that the electroventilation stimulus is gradually withdrawn over a period of time to wean the patient from electroventilator 14. For example, the duration of the time period in which respiration must be sensed or an electroventilation stimulus applied can gradually be lengthened. Alternatively, an electroventilation stimulus would be applied only if the respiration rate falls to some percentage of the normal rate, such as 50%. In other words, the decision making process which determines when an electroventilation stimulus is applied can be altered in a systematic way over time to gradually withdraw ventilatory support. The critical difference between the weaning and demand modes is that in the weaning mode, the criteria for initiating electroventilation are programmed to change gradually during the course of the weaning period.

Physiologically, the appropriate stimulus for tetanizing skeletal muscle is one that repeats often enough so that relaxation does not occur between stimuli. A frequency of 60 pulses/sec has been found to provide a smooth tetanic contraction. A slightly lower frequency is used to stimulate the phrenic nerve to contract the diaphragm.

The duration of each pulse in the train of 60 Hz stimuli merits special consideration because it is desired to avoid stimulating the heart. The theoretical discussion already presented indicates the use of very short-duration pulses such as 0.03 msec pulses.

In normal breathing, inspiration is brought about by tetanic contraction of the inspiratory muscles. During inspiration, more and more inspiratory-muscle motor nerves are recruited, resulting in a smooth inspiration. Expiration results from a sudden cessation of the motor-nerve stimulation and passive recoil of the thoracic cage. FIG. 9 illustrates the volume of air breathed and a typical electromyogram of respiratory muscles, showing that the frequency of stimulation is maximal at maximal inspiration.

There are several ways to configure the stimuli to obtain the smoothest and most efficient movement of air into the trachea. One such method is to configure electroventilator 14 so that stimulator module 16 produces a sudden onset pulse train wherein each pulse has the same amplitude such as pulse train 31 shown in FIG. 10. Although this type of pulse train is effective, it is not optimum.

The inventors have found that a linearly ramped pulse train having a pedestal produces inspiration which is closer to natural inspiration. By pedestal, it is meant that the first pulse has an amplitude at least equal to that necessary to stimulate inhalation, illustratively around 10 ma. Referring to FIG. 11, a linearly ramped pulse train 33 is shown. Pulse train 33 illustratively has a pedestal (first pulse amplitude) of 25% of the final current at the end of the pulse train. Illustratively, the amplitude of the last pulse is 100% of the peak current required, which illustratively ranges from 100 ma.-200 ma. Shorter duration pulses require higher currents as shown in FIG. 1, i.e., about 1000-2000 ma. for 0.01 msec. pulses. The duration of each pulse is in the range of 0.01 msec to 0.1 msec, illustratively 0.03 msec, and the repetition rate of the pulses are illustratively 60 pulses per second. The pulse train illustratively has a burst length or total duration of 0.5 to two seconds and a burst period in the range of 3-12 seconds. The inventors have found linearly ramped pulse trains to be particularly advantageous in stimulating smooth, natural inhalatory effort.

The inventors have also found that a frequency modulated pulse train, such as pulse train 34 shown in FIG. 12, produces inspiration which is more natural than that produced by the sudden onset, uniform amplitude and frequency pulse train shown in FIG. 10. Referring to FIG. 12, frequency pulse train 34 illustratively has an overall duration of one second and each individual pulse has a duration in the range of 0.01 msec to 0.1 msec, illustratively, 0.03 msec. The amplitude of each pulse is illustratively 50-200 ma. D.C. and the frequency of the pulses varies between 10 pulses/sec. to 100 pulses/sec. Illustratively, the beginning frequency is 20 pulses/sec which linearly increases to 60 pulses/sec. The inventors have found frequency modulated pulse trains to be similarly advantageous to linearly, ramped pulse trains.

There are several potential applications of electroventilation in clinical medicine. In the emergency department, the electroventilator may be convenient for treating respiratory depression from sedative drug overdose. In the post-operative setting, electroventilation offers potential as a rapidly and easily applied means to assist ventilation and to prevent or reverse atelectasis. Further, a demand electroventilator can sense improper ventilation or respiration and provide stimuli to correct the condition.

The electroventilator described herein has significant safety aspects. For example, because of the difference in the membrane time constants of cardiac muscle (2 msec) and motor nerves (0.01 msec), the strength-duration curves for stimulation differ. The strength-duration curve for cardiac muscle rises above rheobase at a longer stimulus duration than does that for motor nerve. Therefore, the choice of a very short-duration pulse for electroventilation minimizes the risk of encountering cardiac arrhythmias. To date, cardiac arrhythmia in dogs has not been encountered. An even wider safety margin may be secured by using stimuli shorter than 100 usec for electroventilation. Thus, it can be seen, that the above described demand electroventilator proves advantageous in the treatment and care of those with certain respiratory problems in much the same way that a demand cardiac pacemaker is advantageous in the treatment and care of those with certain heart problems.

Although the invention has been described in detail with reference to certain preferred embodiments and specific examples, variations and modifications exist within the scope and spirit of the invention as described and as defined in the following claims.

What is claimed is:

1. A demand electroventilator for providing electroventilation when needed comprising a plurality of electrodes adapted for placement on the skin of a patient, means for monitoring the respiration of the patient by sensing with the electrodes impedance changes caused by respiration and providing a respiration output signal in response thereto, means for stimulating respiration by stimulating at least one of the respiratory nerves and respiratory muscles of the patient by applying a train of electrical pulses to the patient through the electrodes including means for generating a train of electrical pulses wherein each pulse has a duration of 0.1 msec or less, means for coupling the electrodes both to the stimulating means and to the monitoring means, control means for determining in response to the respiration output signal when it is necessary to stimulate respiration and causing the stimulating means to stimulate respiration in response thereto, means for coupling the control means to the monitoring means, and means for coupling the stimulating means to the control means.

2. The apparatus of claim 1 wherein the control means includes means for determining a level of respiration based upon the respiration output signal and causing the stimulating means to stimulate respiration when the respiration level has fallen below a predetermined level for a predetermined time.

3. The apparatus of claim 1 and further including alarm means, means for coupling the alarm means to the control means, the alarm means including means responsive to the respiration output signal for determining that the monitoring of respiration has become ineffective.

4. The apparatus of claim 3 wherein the alarm means includes means responsive to the respiration output signal for determining that electroventilation is ineffective and providing an alarm in response thereto.

5. The apparatus of claim 4 wherein the monitoring means comprises an impedance pneumograph.

6. The apparatus of claim 1 wherein the monitoring means comprises an impedance pneumograph.

7. The apparatus of claim 1 wherein the means for generating the pulse train comprises means for generating a ramped pulse train.

8. The apparatus of claim 7 wherein the means for generating the ramped pulse train includes means for generating a ramped pulse train having a first pulse with an amplitude of sufficient magnitude to stimulate at least one of the respiratory nerves and respiratory muscles of the patient.

9. The apparatus of claim 8 wherein the means for generating the ramped pulse train includes means for generating a ramped pulse train having a duration of about one second wherein each pulse has a duration in the range of 0.01 msec to 0.1 msec and the pulses have a repetition rate in the range of about twenty pulses-per-second to about sixty pulses-per-second.

10. The apparatus of claim 7 wherein the means for generating a ramped pulse train comprises means for generating a linearly ramped pulse train.

11. The apparatus of claim 7 wherein the control means includes means for systemmatically altering over time the determination of when it is necessary to stimulate respiration to wean the patient from electroventilation.

12. The apparatus of claim 1 wherein the control means includes means for systematically altering over time the determination of when it is necessary to stimulate respiration to wean the patient from electroventilation.

13. A method for monitoring and stimulating respiration of a patient by electroventilation when needed comprising the steps of
monitoring the respiration of the patient by sensing with electrodes placed on the skin of the patient impedance changes caused by respiration;
determining when the respiration of the patient needs to be effected based upon the monitored respiration; and
stimulating the respiration of the patient by stimulating at least one of the respiratory nerves and respiratory muscles of the patient by applying a train of electrical pulses to the skin of the patient through said electrodes wherein each pulse has a duration of 0.1 msec or less in response to the determination that the patient's respiration needs to be effected.

14. The method of claim 13 and further including the step of determining when the patient's respiration is improperly responding to stimulation and initiating an alarm in response thereto.

15. The method of claim 14 and further including the step of determining that the patient's respiration is being improperly monitored and initiating an alarm in response thereto.

16. The method of claim 13 wherein the step of applying the train of electrical pulses comprises applying a train of ramped electrical pulses.

17. The method of claim 16 wherein the step of applying the ramped pulse train comprises applying a linearly ramped pulse train wherein each pulse in the pulse train has a duration in the range of 0.01 msec to 0.1 msec.

18. The method of claim 13 wherein the step of determining when the respiration of the patient needs stimulation includes the step of systemmatically altering over time the determination of when the respiration of the patient needs stimulation to wean the patient form electroventilation.

19. An apparatus for monitoring and stimulating respiration of a patient by electroventilation when needed comprising
a plurality of electrodes adapted for placement on the skin of the patient,
an impedance penumograph for monitoring the respiration of the patient by sensing with said electrodes impedance changes caused by the patient's respiration and providing an output signal in response thereto,
means for stimulating the patient's respiration by stimulating at least one of the respiratory nerves and respiratory muscles of the patient including means for generating a train of electrical pulses,
means for coupling said electrodes to the stimulating means and to the impedance penumograph,
control means for determining in response to the respiration output signal produced by the impedance penumograph when it is necessary to stimulate respiration and causing the stimulating means to stimulate respiration when necessary by generating the train of electrical pulses which are applied to the skin of the patient through said electrodes,
means for coupling the control means to the impedance pneunograph and
means for coupling the control means to the stimulating means.

20. The apparatus of claim 19 wherein the means for generating the electrical pulses comprises means for generating a ramped train of electrical pulses wherein each pulse has a duration of 0.1 msec or less.

* * * * *

UNITED STATES PATENT AND TRADEMARK OFFICE
CERTIFICATE OF CORRECTION

PATENT NO. : 4,827,935

DATED : May 9, 1989

INVENTOR(S) : Leslie A. Geddes et al.

It is certified that error appears in the above-identified patent and that said Letters Patent is hereby corrected as shown below:

On the bibliography page, under the heading "Inventors:", please delete "William D. Vorhees, III", and insert therefor --William D. Voorhees, III--;

At column 3, line 58, please delete "preferrably" and insert therefor --preferably--;

At column 3, line 64, please delete "preferrably" and insert therefor --preferably--;

At column 4, line 24, please delete "its" (second occurrence), and insert therefor --it--;

At column 7, line 65, please delete "preferrably" and insert therefor --preferably--; and At column 12, line 36, please delete "form" and insert therefor --from--.

Signed and Sealed this

Third Day of April, 1990

Attest:

HARRY F. MANBECK, JR.

*Attesting Officer*     *Commissioner of Patents and Trademarks*